US012318437B2

(12) United States Patent
Sangareddy et al.

(10) Patent No.: US 12,318,437 B2
(45) Date of Patent: Jun. 3, 2025

(54) VACCINE FORMULATIONS COMPRISING PRESERVATIVE

(71) Applicant: Biological E Limited, Telangana (IN)

(72) Inventors: Veerapandu Sangareddy, Telangana (IN); Rajendar Burki, Telangana (IN); Rajan Sriraman, Telangana (IN); Ramesh Venkat Matur, Telangana (IN); Narender Dev Mantena, Telangana (IN); Mahima Datla, Telangana (IN)

(73) Assignee: Biological E Limited (IN)

( * ) Notice: Subject to any disclaimer, the term of this patent is extended or adjusted under 35 U.S.C. 154(b) by 191 days.

(21) Appl. No.: 17/261,345

(22) PCT Filed: Jul. 19, 2019

(86) PCT No.: PCT/IB2019/056202
§ 371 (c)(1),
(2) Date: Jan. 19, 2021

(87) PCT Pub. No.: WO2020/021416
PCT Pub. Date: Jan. 30, 2020

(65) Prior Publication Data
US 2021/0322533 A1 Oct. 21, 2021

(30) Foreign Application Priority Data
Jul. 21, 2018 (IN) .............................. 201841027285

(51) Int. Cl.
*A61K 39/09* (2006.01)
*A61K 39/00* (2006.01)
(52) U.S. Cl.
CPC ............ *A61K 39/092* (2013.01); *A61K 39/00* (2013.01)
(58) Field of Classification Search
None
See application file for complete search history.

(56) References Cited

U.S. PATENT DOCUMENTS

| 6,790,445 B1 * | 9/2004 | Ng ........................ A61K 47/183 |
| | | 424/189.1 |
| 9,095,567 B2 * | 8/2015 | Khandke ................. A61P 31/04 |
| 2004/0258700 A1 | 12/2004 | Frimann |
| 2013/0273098 A1 | 10/2013 | Blue et al. |

FOREIGN PATENT DOCUMENTS

| CN | 101785857 A | 7/2010 | |
| JP | 2006526649 A | 11/2006 | |
| JP | 2004524320 A | 3/2008 | |
| WO | WO-2013103144 A1 * | 7/2013 | ........ B01L 3/502753 |
| WO | WO 2018/064444 | 4/2018 | |
| WO | WO 2018/169303 | 9/2018 | |

OTHER PUBLICATIONS

Skinner et al. Vaccine, vol. 29, No. 48 Nov. 2011., (Year: 2011).*
Khandke et al., Vaccine, vol. 29, pp. 7144-7153, 2011 (Year: 2011).*
Peter Masucci, The Journal of Infectious Disease vol. 30, No. 4, pp. 379-367, 1992. (Year: 1992).*
Denyer et al., "Synergy in preservative combinations," International Journal of Pharmaceutics, 25:245-253 (1985).
Hilliard et al., "Preservatives for Poliomyelitis (Salk) Vaccine III 2-Phenoxyethanol," Journal of Pharmaceutical Sciences, 53(8):899-901 (1964).
International Search Report and Written Opinion dated Oct. 12, 2019 for International Application No. PCT/IB2019/056202.
Skinner et al., "Pre-clinical evaluation of a 15-valent pneumococcal conjugate vaccine (PCV15-CRM197) in an infant-rhesus monkey immunogenicity model," Vaccine, 29(48):8870-6 (publication date: Nov. 8, 2011).

* cited by examiner

*Primary Examiner* — Jana A Hines
*Assistant Examiner* — Khatol S Shahnan Shah
(74) *Attorney, Agent, or Firm* — Perkins Coie LLP

(57) ABSTRACT

The present invention relates to vaccine formulations comprising preservative systems. More particularly, the present invention relates to preservative systems for vaccine formulations which is free of thiomersal, and comprising 2-phenoxyethanol and at least one other preservative selected from m-cresol, benzyl alcohol, phenol and benzoic acid.

10 Claims, 3 Drawing Sheets

VACCINE FORMULATIONS COMPRISING PRESERVATIVE

TECHNICAL FIELD

The present invention relates to preservative system and use thereof in vaccine formulations. More particularly, the present invention relates to mono or multivalent vaccine formulations comprising preservative system and which is free of thiomersal.

BACKGROUND

Vaccine is a biological preparation that provides active acquired immunity to a particular disease. A vaccine typically contains an agent that resembles a disease-causing microorganism and is often made from attenuated or killed forms of the microbe, its toxins, or at least one of its surface proteins or at least one of its capsular polysaccharides. The agent stimulates the body's immune system to recognize the agent as a threat, destroy it, recognize and destroy any of these microorganisms that it later encounters. Besides from having a certain level of immunogenicity, potency, stability, a vaccine formulation needs to be free from microbial contamination.

Preservatives are required for multidose vaccine formulations to prevent contamination and to stabilize the composition of subsequent doses after the first dose is used. The preservative must enable the vaccine formulation to pass efficacy tests or antimicrobial challenge tests.

U.S. Pat. No. 6,790,445 B1 discloses combinations of preservatives that pass antimicrobial testing requirements for United States Pharmacopeia (USP), British Pharmacopeia (BP), and European Pharmacopeia (EP) selected from the group consisting of (1) 1.5% benzyl alcohol; (2) 0.225% methyl paraben sodium, 0.025% propyl paraben sodium; and 0.9% benzyl alcohol, and (3) 0.225% methyl paraben sodium, 0.025% propyl paraben sodium, and 0.375% 2-phenoxyethanol.

U.S. Pat. No. 9,095,567 B2 describes a multivalent immunogenic composition comprising a polysaccharide-protein conjugates consisting of pneumococcal capsular polysaccharides from Streptococcus pneumoniae serotypes 1, 3, 4, 5, 6A, 6B, 7F, 9V, 14, 18C, 19A, 19F and 23F, individually conjugated to $CRM_{197}$, and further comprising not less than 7 mg/mL of 2-phenoxyethanol (2-PE). This patent disclosed that the preservative effectiveness test (PET) results showed that all of the tested preservatives met the USP requirements but not the EP criteria. 2-PE was the only candidate preservative which was found to be safe at higher dosages.

U.S. Patent Publication No. 2004/0258700 A1 discloses a vaccine formulation comprising an immunogen, a preservative characterized in that the preservative is a combination of at least two paraben esters and 2-phenoxyethanol.

U.S. Patent Publication No. 2013/0273098 A1 described that the addition of the surfactant 0.1% Poloxamer 188 (Pluronic F-68) resulted in no observed particulates with any of the preservatives tested such as phenol, 2-phenoxyethanol, m-cresol, benzyl alcohol, or chlorobutanol.

WO Publication No. 2018/169303 A1 discloses a vaccine composition comprising: (i) a capsular polysaccharide-protein conjugate; (ii) 2-phenoxyethanol (2-PE); and (iii) formaldehyde (HCHO), and a method for preparing the same.

Hilliard et. al (1964, Journal of Pharmaceutical Sciences 53(8), 899-901) discloses the addition of 0.375 percent v/v of 2-phenoxyethanol to poliomyelitis vaccine furnished a stable mixture of preservatives (streptomycin, neomycin, and 2-phenoxyethanol) which was inhibitory to both bacteria and fungi.

Stephen et. al., (1985, International Journal of Pharmaceutics, 25, 245-253) discloses antimicrobial preservatives that belong to the same chemical groups are believed to produce merely additive effects when used in combination.

Preservatives generally offer limited protection against viral contamination. Bactericides and fungicides may evince their effects on a variety of microbial cellular targets, for example; the cell wall, the cytoplasmic membrane or the cytoplasm. It is often difficult to assign a precise target for a specific class of preservative; the target can and does change with preservative concentration. As a consequence, preservatives often interfere with several different microbial cellular mechanisms. Such cytotoxicity may also affect mammalian cells. Hence inclusion levels should be minimal, consistent with adequate preservation. There is a regulatory expectation to provide the reason for preservative inclusion, proof of efficacy, safety information, control methods and details of labeling in the finished product.

In concept, the preservative system protects the product against microbial proliferation but does not compromise product performance. In practice, this means that it must:
  exert a wide spectrum of antimicrobial activity at low inclusion levels.
  maintain activity throughout product manufacture, shelf life and usage.
  not compromise the quality or performance of product, pack or delivery system.
  not adversely affect patient safety or tolerance of the product.

Pharmacopoeial antimicrobial effectiveness tests (AET) or preservative efficacy tests (PET) involve challenging a product with a defined number of colony forming units (cfu) of a variety of test microorganisms (bacteria, yeasts and fungi), enumeration at time zero and then monitoring kill/survival rate at defined time intervals. In addition to antimicrobial effectiveness testing (AET), it is a regulatory requirement to monitor the chemical stability of the drug product (in its final container) throughout the product's proposed shelf-life.

Thimerosal (also known as Thiomersal; Merthiolate) is an ethyl mercury-containing preservative which has, since the early 1930s, been added to many multi-dose injectable formulations. Thiomersal, which contains mercury, is claimed to cause autism in children and is also toxic to the environment. It would be advantageous to look for preservatives which are safe for vaccines to replace thimerosal. Thus, there is a need for a vaccine formulation comprising preservatives that are safe as well as effective.

Although the safety profile of 2-phenoxyethanol (2-PE) is better than that of mercurial preservatives (e.g. thiomersal), but it is the weaker antimicrobial of the two and required to be include at higher concentration levels in the vaccine formulations.

Thus, in order to improve the preservative efficacy of 2-PE at low concentration levels in vaccine formulations, inventors of the present invention through their continuous efforts have developed a low concentration of preservative system comprising 2-PE in combination with other preservatives. The inventors have found that the preservative systems are safe and effective for use in vaccine formulations for prevention of microbial/viral growth.

Objective

It is an objective of the present invention to provide a preservative composition comprising low concentration levels of 2-phenoxyethanol for use in vaccine formulations for prevention of microbial/viral growth.

It is another objective of the invention to provide stable multi-dose vaccine formulation that comprises low concentration levels of 2-phenoxyethanol.

SUMMARY

Accordingly, the present invention provides a vaccine formulation comprising a preservative system comprising 2-phenoxyethanol at a concentration in the range of 0.1% to 0.6% and at least one other preservative selected from the group consisting of m-cresol, benzyl alcohol, phenol and benzoic acid.

The invention also provides a vaccine formulation comprising an immunogen, a preservative system comprising 2-phenoxyethanol at a concentration in the range of 0.1% to 0.6% and at least one other preservative selected from the group consisting of m-cresol, benzyl alcohol, phenol and benzoic acid and one more suitable pharmaceutically acceptable excipients.

The invention also provides a process for manufacturing vaccine formulation comprising a preservative system containing 2-phenoxyethanol at a concentration in the range of 0.1% to 0.6% and at least one other preservative selected from the group consisting of m-cresol, benzyl alcohol, phenol and benzoic acid.

The invention also provides a process for manufacturing vaccine formulation comprising preservative system containing 2-phenoxyethanol at a concentration in the range of 0.1% to 0.5% and at least one other preservative selected from the group consisting of at least 0.005% m-cresol, benzyl alcohol, phenol and benzoic acid.

DEFINITIONS

Figure 1:
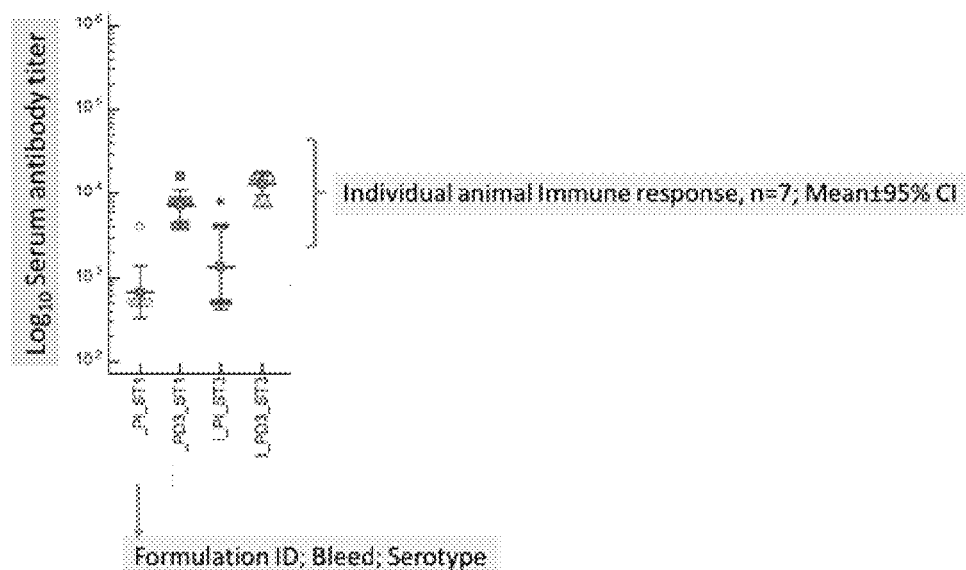
FIG. 1 depicts plot layout of serum antibody titers in rabbit.

Embodiments described herein can be understood more readily by reference to the following detailed description, examples, and drawings. Elements, apparatus and methods described herein are merely illustrative of the principles of the present invention and are not limited to the specific embodiments presented in the detailed description, examples, and drawings. Numerous modifications and adaptations will be readily apparent to those of skill in the art without departing from the spirit and scope of the invention.

Unless defined otherwise, all technical and scientific terms used herein have the same meaning as commonly understood by one of ordinary skill in the art to which the methods belong. Although any combinations, compositions or methods similar or equivalent to those described herein can also be used in the practice or testing of the embodiments of the present invention, representative illustrative methods and compositions are now described.

It is appreciated that certain features of the methods, which are, for clarity, described in the context of separate embodiments, may also be provided in combination in a single embodiment. Conversely, various features of the methods and compositions, which are, for brevity, described in the context of a single embodiment, may also be provided separately or in any suitable sub-combination. It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation. The term "at least one" means one and more than one.

As will be apparent to those of skill in the art upon reading this disclosure, each of the individual embodiments described and illustrated herein has discrete components and features which may be readily separated from or combined with the features of any of the other embodiments without departing from the scope or spirit of the present methods. Any recited method can be carried out in the order of events recited or in any other order that is logically possible.

As used herein, the terms "preservative system" or "preservative composition" are interchangeable and refers to a mixture or composition that is added to a vaccine composition or formulation to prevent decomposition due to chemical change or microbial/viral contamination. In the context of the invention preservative system refers to a composition comprising 2-phenoxyethanol and at least one other preservative selected from the group consisting of m-cresol, benzyl alcohol, phenol and benzoic acid.

The term "immunogen or an antigen" refers to a substance which stimulates the production of an antibody or elicits a immoral and/or cellular immune response resulting in immunity of the host towards the pathogen.

As used herein, the term "monovalent vaccine" refers to a vaccine having one principal antigenic component.

As used herein, the term "multivalent vaccine" refers to a vaccine comprising more than one antigenic component. The term includes combination vaccine, bivalent vaccines, trivalent vaccines, tetravalent vaccines, pentavalent vaccines, hexavalent vaccines and the like.

As used herein, the term "Vi:O2" refers to a bivalent vaccine formulation against typhoid and paratyphoid comprising antigens from *Salmonella typhi* and *Salmonella paratyphi*.

As used herein, the term "MR" refers to a bivalent vaccine formulation against measles and rubella.

As used herein the term "Td" refers to Diphtheria and Tetanus Vaccine [Adsorbed, Reduced Antigen(s) content].

As used herein, the term "DTwP" refers to a trivalent vaccine formulation against diphtheria, tetanus and whole-cell pertussis.

As used herein, the term "Vi:O2-HepA" refers to a trivalent vaccine formulation against typhoid, paratyphoid and Hepatitis A.

As used herein, the term "MMR" refers to a trivalent vaccine formulation against measles, mumps and rubella.

As used herein, the term "DTwP-Hib" refers to a tetravalent vaccine formulation against diphtheria, tetanus, whole-cell pertussis and *Haemophilus influenzae* type b.

As used herein, the term "DTaP-Hib" refers to a tetravalent vaccine formulation against diphtheria, tetanus, acellular pertussis and *Haemophilus influenzae* type b.

As used herein, the term "DTwP-IPV" refers to a tetravalent vaccine formulation against diphtheria, tetanus, whole-cell pertussis and inactivated polio virus.

As used herein, the term "DTwP-HepB" refers to a tetravalent vaccine formulation against diphtheria, tetanus, whole-cell pertussis and hepatitis B.

As used herein, the term "ACW-135XY" refers to a pentavalent conjugate vaccine formulation against meningococcal group A, C, W-135, X and Y.

As used herein, the term "DtwPHib-HepB" refers to a pentavalent vaccine formulation against diphtheria, tetanus, whole-cell pertussis, *Haemophilus influenzae* type b and hepatitis B.

As used herein, the term "DtaPHib-HepB" refers to a pentavalent vaccine formulation against diphtheria, tetanus, acellular pertussis, *Haemophilus influenzae* type b and hepatitis B.

As used herein, the term "DtwPHib-HepB-IPV" refers to a hexavalent vaccine formulation against diphtheria, tetanus, whole-cell pertussis, *Haemophilus influenzae* type b, hepatitis B and inactivated polio virus.

As used herein, the term "DtaPHib-HepB-IPV" refers to a hexavalent vaccine formulation against diphtheria, tetanus, acellular pertussis, *Haemophilus influenzae* type b, hepatitis B and inactivated polio virus.

As used herein, the term "pharmaceutically acceptable carrier(s)" refers to one or more optional components which may be added to the vaccine formulation for administration of the antigens and/or viruses which does not itself induce the production of antibodies harmful to the individual receiving the composition, and which may be administered without undue toxicity. The term includes one or more excipient, adjuvants, diluents, buffers or surfactants, or a combination thereof. By pharmaceutically acceptable or pharmacologically acceptable is meant a material which is not biologically or otherwise undesirable, i.e., the material may be administered to an individual in a formulation or composition without causing any undesirable biological effects or interacting in a deleterious manner with any of the components of the composition in which it is contained.

As used herein, the phrase "microbial or viral contamination" refers to undesired growth of microbes or viruses in vaccine formulation.

DETAILED DESCRIPTION

As used herein the vaccine or immunogen of the present invention includes pneumococcal conjugate, meningococcal conjugate, typhoid conjugate, paratyphoid conjugate, Hib conjugate and multivalent vaccine comprising one or more antigens selected from Measles (M), Mumps (M), Rubella (R), Hepatitis A Virus (HAV), Hepatitis C Virus (HCV), Diphtheria (D), Tetanus (T), whole cell (wP) or acellular Pertussis (aP), Hib Polysaccharide, Hepatitis B (HepB) and Inactivated Poliomyelitis Virus (IPV).

Monovalent vaccines includes antigens selected or isolated from *Streptococcus pneumonia* (Pneumococcal capsular polysaccharide), *Neisseria meningitides* (Men A, C, W-135 or Y), *Salmonella typhi* (Vi), *Salmonella paratyphi* (0:2), *Haemophilus influenza* (Hib-PRP), *Corynebacterium* Diptheriae (Diptheriae Toxoid-DT), *Bordetella pertussis* (wP/aP), *Clostridium tetani* (Tetanus Toxoid), Hepatitis A Virus (HAV), Hepatitis B Virus (HBV), Hepatitis C Virus (HCV), Inactivated Japanese Encephalitis Virus, Rabies Virus and Inactivated Poliomyelitis Virus.

Multivalent vaccine includes bivalent, trivalent, tetravalent, Pentavalent and Hexavalent such as DT (Diptheriae Toxoid), MR (Measles and Rubella Vaccine), Vi:O2 (*Salmonella typhi* and *Salmonella paratyphi*) conjugate, Vi:O2-HepA (*Salmonella typhi, Salmonella paratyphi* and Hepatitis A vaccine), MMR (Measles, Mumps, and Rubella vaccine), DTwP vaccine (vaccine against diphtheria, tetanus and whole-cell pertussis), ACW-135XY (Conjugate vaccine against meningococcal group A, C, W-135, X and Y), DTwP-Hib (Vaccine against diphtheria, tetanus, whole-cell pertussis and *Haemophilus influenzae* type b), DTaP-Hib (Diphtheria, Tetanus, Acellular Pertussis and *Haemophilus influenzae* type b), DTwP-HepB (Vaccine against diphtheria, tetanus, whole-cell pertussis and hepatitis B), DTwPHib-HepB (Vaccine against diphtheria, tetanus, whole-cell pertussis, *Haemophilus influenzae* type b and hepatitis B), DTaPHib-HepB (Diphtheria, Tetanus, Acellular Pertussis, *Haemophilus influenzae* type b and hepatitis B), DTwP-IPV (Vaccine against diphtheria, tetanus, whole-cell pertussis and inactivated polio virus), DTwPHib-HepB-IPV (Vaccine against diphtheria, tetanus, whole-cell pertussis, *Haemophilus influenzae* type b, hepatitis B and inactivated polio virus), DTaPHib-HepB-IPV (Vaccine against diphtheria, tetanus, acellular pertussis, *Haemophilus influenzae* type b, hepatitis B and inactivated polio virus).

The percentage of concentration (%) as used herein is weight by volume (w/v) or weight by weight (w/w).

The present invention provides mono and multivalent combination vaccine formulation comprising preservative system containing 2-phenoxyethanol at a concentration in the range of 0.1% to 0.6% and at least one other preservative selected from the group consisting of m-cresol, benzyl alcohol, phenol and benzoic acid.

In an embodiment, the present invention provides pneumococcal capsular polysaccharide protein conjugate vaccine formulation comprising one or more pneumococcal polysaccharide protein conjugates and a preservative system containing 2-phenoxyethanol at a concentration in the range of 0.1% to 0.6% and at least one other preservative selected from the group consisting of m-cresol, benzyl alcohol, phenol and benzoic acid and one or more pharmaceutically acceptable carriers or excipients.

In yet another embodiment, the present invention provides meningococcal conjugate vaccine formulation comprising *N. meningitidis* serogroup A, C, W-135, X and Y capsular polysaccharide antigens individually conjugated to carrier protein and a preservative system containing 2-phenoxyethanol at a concentration in the range of 0.1% to 0.6% and at least one other preservative selected from the group consisting of m-cresol, benzyl alcohol, phenol and benzoic acid and one or more pharmaceutically acceptable carriers or excipients.

In yet another embodiment, the present invention provides typhoid conjugate vaccine formulation comprising Vi polysaccharide conjugated to carrier protein and a preservative system containing 2-phenoxyethanol at a concentration in the range of 0.1% to 0.6% and at least one other preservative selected from the group consisting of m-cresol, benzyl alcohol, phenol and benzoic acid and one or more pharmaceutically acceptable carriers or excipients.

In yet another embodiment, the present invention provides paratyphoid conjugate vaccine formulation comprising O:2 polysaccharide conjugated to carrier protein and a preservative system containing 2-phenoxyethanol at a concentration in the range of 0.1% to 0.6% and at least one other preservative selected from the group consisting of m-cresol, benzyl alcohol, phenol and benzoic acid and one or more pharmaceutically acceptable carriers or excipients.

In yet another embodiment, the present invention provides Hib conjugate vaccine formulation comprising polyribosylribitol phosphate (PRP) capsular polysaccharide conjugated to carrier protein and a preservative system containing 2-phenoxyethanol at a concentration in the range of 0.1% to 0.6% and at least one other preservative selected from the group consisting of m-cresol, benzyl alcohol, phenol and benzoic acid and one or more pharmaceutically acceptable carriers or excipients.

In an embodiment, the present invention provides a pneumococcal capsular polysaccharide protein conjugate vaccine formulation comprising one or more pneumococcal polysaccharide protein conjugates and a preservative system containing 2-phenoxyethanol at a concentration of 0.1% to 0.6% and at least one other preservative selected from the group consisting of m-cresol, benzyl alcohol, phenol and benzoic acid at a concentration of 0.005% to 0.3% and one or more pharmaceutically acceptable carriers.

The carrier protein according to the present invention is selected from the group consisting of $CRM_{197}$, PspA, PsaA, Protein D, diphtheria toxoid (DT), tetanus toxoid (TT) and the like or combination thereof.

Pneumococcal conjugate vaccine according to the present invention includes one or more capsular polysaccharides from *Streptococcus pneumonia* serotype selected from *Streptococcus pneumonia* serotypes 1, 2, 3, 4, 5, 6A, 6B, 6C, 6D, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45 wherein each polysaccharide is conjugated to a carrier protein preferably selected from PsaA, $CRM_{197}$, inactivated bacterial toxins such as diphtheria toxoid (DT), tetanus toxoid (TT), pertussis toxoid, cholera toxoid, or *Haemophilus influenzae* protein D or combination thereof and a preservative system containing 2-phenoxyethanol at a concentration in the range of 0.1% to 0.6% and at least one other preservative selected from the group consisting of m-cresol, benzyl alcohol, phenol, benzoic acid and one or more pharmaceutically acceptable carriers.

In an embodiment, the present invention provides a pneumococcal conjugate vaccine formulation comprising pneumococcal capsular polysaccharides wherein each polysaccharide is selected from *Streptococcus pneumonia* serotypes 1, 2, 3, 4, 5, 6A, 6B, 6C, 6D, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39, and 45 conjugated to a carrier protein and a preservative system containing 2-phenoxyethanol at a concentration in the range of 0.1% to 0.6% and at least one other preservative selected from the group consisting of m-cresol, benzyl alcohol, phenol and benzoic acid.

In an embodiment, the present invention provides a pneumococcal conjugate vaccine formulation comprising pneumococcal capsular polysaccharides wherein each polysaccharide is selected from *Streptococcus pneumonia* serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45 conjugated to a carrier protein and a preservative system containing 2-phenoxyethanol at a concentration in the range of 0.1% to 0.6% and at least one other preservative selected from the group consisting of 0.005% to 0.3% of m-cresol, 0.01% to 1% of benzyl alcohol, 0.01% to 1% of benzoic acid by weight of the vaccine formulation.

Pneumococcal capsular polysaccharide protein conjugate vaccine according to the present invention is a multivalent immunogenic composition such as 10 valent, 13 valent, 14 valent, 15 valent, 16 valent, 17 valent, 18 valent, 19 valent, 20 valent, 22 valent, 23 valent, 24 valent, 25 valent or 26 valent pneumococcal vaccine composition.

In an embodiment, Pneumococcal capsular polysaccharide protein conjugate vaccine according to the present invention is a 14 valent immunogenic composition comprising capsular polysaccharides from *Streptococcus pneumoniae* serotypes 1, 3, 4, 5, 6B, 7F, 9V, 14, 18C, 19A, 19F, 22F, 23F and 33F.

In yet another embodiment, Pneumococcal capsular polysaccharide protein conjugate vaccine according to the present invention is a 20 valent immunogenic composition comprising capsular polysaccharides from *Streptococcus pneumoniae* serotypes 1, 3, 4, 5, 6A, 6B, 6C/6D, 7F, 9V, 11A, 12F, 14, 15A, 18C, 19A, 19F, 22F, 23A, 23F and 35B.

In yet another embodiment, Pneumococcal capsular polysaccharide protein conjugate vaccine according to the present invention is 20 valent immunogenic composition comprising capsular polysaccharides from *Streptococcus pneumoniae* serotypes 1, 3, 4, 5, 6A, 6B, 6C/6D, 7F, 9V, 14, 15A, 15C, 18C, 19A, 19F, 23A, 23B, 23F, 24F and 35B.

In yet another embodiment, Pneumococcal capsular polysaccharide protein conjugate vaccine according to the present invention is a 24 valent immunogenic composition comprising capsular polysaccharides from *Streptococcus pneumoniae* serotypes 1, 3, 4, 5, 6A, 6B, 7F, 8, 9V, 10A, 11A, 12F, 14, 15A, 18C, 19A, 19F, 22F. 23A, 23B, 23F, 24F, 33F and 35B.

In an embodiment, the present invention provides a pneumococcal conjugate vaccine formulation comprising pneumococcal capsular polysaccharides wherein each polysaccharide is selected from *Streptococcus pneumonia* serotypes 1, 3, 4, 5, 6B, 7F, 9V, 14, 18C, 19A, 19F, 22F, 23F and 33F conjugated to a carrier protein and a preservative system containing 2-phenoxyethanol at a concentration in the range of 0.1% to 0.6% and at least one other preservative selected from the group consisting of 0.005% to 0.3% of m-cresol, 0.01% to 1% of benzyl alcohol, 0.01% to 1% of benzoic acid by weight of the vaccine formulation.

In yet another embodiment, the present invention provides a pneumococcal conjugate vaccine formulation comprising pneumococcal capsular polysaccharides wherein each polysaccharide is selected from *Streptococcus pneumonia* serotypes 1, 3, 4, 5, 6B, 7F, 9V, 14, 18C, 19A, 19F, 22F, 23F and 33F conjugated to a carrier protein and a preservative system containing 2-phenoxyethanol at a concentration in the range of 0.1% to 0.5% and at least one other preservative selected from the group consisting of 0.005% to 0.3% of m-cresol, 0.01% to 1% of benzyl alcohol, 0.01% to 1% of benzoic acid by weight of the vaccine formulation.

The carrier protein according to the present invention is preferably protein that is non-toxic and non-reactogenic and obtainable in sufficient amount and is selected from PsaA, $CRM_{197}$, inactivated bacterial toxins such as diphtheria toxoid (DT), tetanus toxoid (TT), pertussis toxoid, cholera toxoid, exotoxin A from *Pseudomonas aeruginosa*, bacterial outer membrane proteins such as outer membrane complex C (OMPC), porins, transferrin binding proteins, pneumolysin, PspA, C5a peptidase from Group A or Group B *streptococcus*, or *Haemophilus influenzae* protein D, ovalbumin, keyhole limpet hemocyanin (KLH), bovine serum albumin (BSA) and purified protein derivative of tuberculin (PPD) and combination thereof. For examples, some polysaccharides are conjugated to $CRM_{197}$ as carrier protein and some polysaccharides are conjugated to PsaA or DT or TT and the like.

In yet another embodiment, the present invention provides a multidose polysaccharide protein conjugate vaccine formulation comprising a preservative system containing 2-phenoxyethanol at a concentration in the range of 0.1% to 0.5% and at least one other preservative selected from the group consisting of m-cresol, benzyl alcohol, phenol and benzoic acid and a pharmaceutically acceptable vehicle and one or more pharmaceutically acceptable excipients/adjuvants.

In yet another embodiment, the present invention provides conjugate vaccine formulation comprising a preservative system containing 2-phenoxyethanol at a concentration in the range of 0.1% to 0.6% and at least one other preservative selected from the group consisting of 0.005% to 0.3% of m-cresol, 0.01% to 1% of benzyl alcohol, 0.01% to 1% of benzoic acid by weight of the vaccine formulation and a pharmaceutically acceptable vehicle and one or more pharmaceutically acceptable excipients/adjuvants.

A composition according to the present invention may be manufactured conventionally. In particular, it may be formulated with a pharmaceutically acceptable carrier, diluent or excipient, e.g. water, buffered saline, glycerol, propylene glycol and dextrose solution. In addition, the composition may contain buffer such as sodium phosphate, potassium phosphate, sodium succinate, histidine and the like; or a stabilizer, polysorbate, MPLA (monophosphoryl lipid A), and the like; an adjuvant such as an aluminum compound, e.g. an aluminium hydroxide, an aluminium phosphate or an aluminium hydroxyphosphate, and, a lyophilization excipient. In general, these ingredients/carriers may be selected as a function of the mode and route of administration and based on standard pharmaceutical practices.

The composition of the present invention is formulated as multiple dose vial.

In yet another embodiment, the present invention provides a method of preserving vaccine formulation, which method comprises, mixing vaccine solution and one or more excipients such as an adjuvants, diluents, buffers or surfactants with a preservative system containing 2-phenoxyethanol at a concentration in the range of 0.1% to 0.5% and at least one other preservative selected from the group consisting of m-cresol, benzyl alcohol, phenol and benzoic acid to form a mixture of vaccine solution and preservative.

In a preferred embodiment, the present invention provides a vaccine formulation comprising a preservative system containing 2-phenoxyethanol at a concentration in the range of 0.1% to 0.5% and at least one other preservative selected from the group consisting of 0.005% to 0.3% of m-cresol, 0.01% to 1% of benzyl alcohol, 0.01% to 1% of benzoic acid and a pharmaceutically acceptable vehicle and one or more pharmaceutically acceptable excipients/adjuvants. The pharmaceutically acceptable excipients or adjuvants may be selected from group of adjuvants such as aluminum hydroxide, aluminum phosphate, surfactants such as polysorbate 20, polysorbate 80, poloxamers, vehicles, solvents or co-solvents such as soyabean oils, PEG, stabilizers such as EDTA and may include antioxidants such as polyphenols, Tocopheryl Polyethylene Glycol Succinate (TPGS). The pH of the vaccine formulation according to the present invention is adjusted to maintain between 4.0 to 8.0.

In another preferred embodiment, the present invention provides a vaccine formulation comprising 0.3% to 0.4% of 2-PE and 0.1% to 0.3% of m-cresol as preservative and one or more pharmaceutically acceptable carrier or excipient.

In another preferred embodiment, the present invention provides a vaccine formulation comprising 0.1% to 0.4% of 2-PE and 0.01% to 0.05% m-cresol as preservative and one or more pharmaceutically acceptable carrier or excipient.

In another preferred embodiment, the present invention provides a 14 valent pneumococcal conjugate vaccine formulation comprising:

a) capsular polysaccharide selected from *Streptococcus pneumoniae* serotypes 1, 3, 4, 5, 6B, 7F, 9V, 14, 18C, 19A, 19F, 22F, 23F and 33F individually conjugated to carrier protein selected from $CRM_{197}$, pneumococcal surface protein A (PspA), pneumococcal adhesin protein (PsaA) or combination thereof, b) a preservative system containing 0.1% to 0.4% of 2-PE and 0.005% to 0.3% of m-cresol and c) one or more pharmaceutically acceptable carrier or excipient.

In preferred embodiment, the present invention provides a 20 valent pneumococcal conjugate vaccine formulation comprising:

a) capsular polysaccharide selected from *Streptococcus pneumoniae* serotypes 1, 3, 4, 5, 6A, 6B, 6C/6D, 7F, 9V, 11A, 12F, 14, 15A, 18C, 19A, 19F, 22F, 23A, 23F and 35B individually conjugated to carrier protein selected from $CRM_{197}$, pneumococcal surface protein A (PspA), pneumococcal adhesin protein (PsaA) or combination thereof, b) a preservative system containing 0.1% to 0.4% of 2-PE and 0.005% to 0.1% of m-cresol and c) one or more pharmaceutically acceptable carrier or excipient.

In preferred embodiment, the present invention provides a 24 valent pneumococcal conjugate vaccine formulation comprising:

a) capsular polysaccharide selected from *Streptococcus pneumoniae* serotypes 1, 3, 4, 5, 6A, 6B, 7F, 8, 9V, 10A, 11A, 12F, 14, 15A, 18C, 19A, 19F, 22F. 23A, 23B, 23F, 24F, 33F and 35B individually conjugated to carrier protein selected from $CRM_{197}$, pneumococcal surface protein A (PspA), pneumococcal adhesin protein (PsaA) or combination thereof, b) a preservative system containing 0.1% to 0.4% of 2-PE and 0.005% to 0.1% of m-cresol and c) one or more pharmaceutically acceptable carrier or excipient.

The amount of pneumococcal conjugate in each vaccine dose is selected as an amount that induces an immunoprotective response without significant, adverse effects. Such an amount may vary depending upon the pneumococcal serotype. Each 0.5 mL dose is formulated to contain: 2 to 4 µg of each polysaccharide; about 30-70 µg $CRM_{197}$ carrier protein.

In another preferred embodiment the present invention provides a conjugate vaccine formulation comprising polysaccharide protein conjugate vaccine selected from the group consisting of pneumococcal conjugate, meningococcal conjugate, typhoid conjugate, paratyphoid or Hib conjugate and a preservative system containing 0.1% to 0.4% 2-PE and 0.01% to 0.3% m-cresol and one or more pharmaceutically acceptable carrier or excipient.

In yet another embodiment, the present invention provides a pneumococcal conjugate vaccine formulation comprising pneumococcal capsular polysaccharides wherein each polysaccharide is selected from *Streptococcus pneumonia* serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39, and 45 conjugated to a carrier protein and a preservative system containing 0.1 to 0.5% of 2-phenoxyethanol at a concentration in the range of and 0.01% to 0.3% of m-cresol by weight of the vaccine formulation.

Compositions of the present invention may be administered to a subject in need thereof by conventional routes used in the field of vaccines. For example, compositions of the present invention may be administered systemically, such as parenterally (e.g. subcutaneously, intramuscularly, intradermally and/or intravenously) or mucosally (e.g., orally and/or nasally).

In some embodiments, the present invention also provides methods of inducing an immune response in a subject in need thereof. The methods for inducing the immune response comprise administering an immunologically effective amount of the vaccine composition described herein to the subject in need thereof.

According to the methods of the present invention, the subject to whom the compositions described herein to be administered is a human, such as an infant (less than about 1 year of age), a toddler (about 12 months to about 24 months of age), a young child (about 2 years to about 5 years of age), an older child (about 5 years to about 13 years of age), an adolescent (about 13 years to about 18 years of age), an adult (about 18 years to about 65 years of age), or an elder (more than about 65 years of age).

In another preferred embodiment, the present invention provides an immunogenic composition of pneumococcal conjugate vaccine comprising 0.1% to 0.4% of 2-PE and 0.01% to 0.3% of m-cresol and one or more pharmaceutically acceptable vehicle and one or more pharmaceutically acceptable excipients/adjuvants.

In another preferred embodiment, the present invention provides an immunogenic composition of meningococcal conjugate vaccine comprising 0.3% to 0.4% of 2-PE and 0.1% to 0.3% of m-cresol and one or more pharmaceutically acceptable vehicle and one or more pharmaceutically acceptable excipients/adjuvants.

In another preferred embodiment, the present invention provides an immunogenic composition of typhoid conjugate vaccine comprising 0.3% to 0.4% of 2-PE and 0.1% to 0.3% of m-cresol and one or more pharmaceutically acceptable vehicle and one or more pharmaceutically acceptable excipients/adjuvants.

In another preferred embodiment, the present invention provides an immunogenic composition of paratyphoid vaccine comprising 0.3% to 0.4% of 2-PE and 0.1% to 0.3% of m-cresol and one or more pharmaceutically acceptable vehicle and one or more pharmaceutically acceptable excipients/adjuvants In another preferred embodiment, the present invention provides an immunogenic composition of Hib conjugate vaccine comprising 0.3% to 0.4% of 2-PE and 0.1% to 0.3% of m-cresol and one or more pharmaceutically acceptable vehicle and one or more pharmaceutically acceptable excipients/adjuvants.

Preservative efficacy in medicines is typically investigated using challenge tests. In such tests, the product is artificially contaminated with a high concentration of standard bacterial and fungal test strains. The rate and extent of reductions in inoculum viability over a specified period forms the basis for acceptance/rejection of preservative efficacy.

The efficacy of 2-phenoxyethanol (2-PE) and m-cresol preservative composition with least yet effective dose when tested has shown strong microbicidal activity against Gram-positive bacteria, Gram-negative bacteria, yeast and fungi.

BIOBALL® (manufactured by BTF Pty Ltd.) is a small water-soluble ball containing a precise number of microorganisms delivering unprecedented accuracy for quantitative microbiological quality control.

Compositions of the invention can be prepared using conventional techniques which involves dissolving and mixing the ingredients as appropriate to give the desired end product.

EXAMPLES

The following examples are provided to illustrate the disclosure and are merely for illustrative purpose only and should not be construed to limit the scope of the disclosure.

Example 1: Detailed Study of the Preservative Selection and Efficacy Study

The aim of the study was to establish the least concentration of preservative which is susceptible to bacteria and fungi that can be used in the formulation of vaccines, specifically Pneumococcal Conjugate Vaccine (PCV). Two types of preservatives with different concentrations were chosen for the study. The test cultures were received in the form of Bioball® (manufactured by BTF Pty Ltd.) from which the preparation of glycerol aliquots was carried out.

In this study, the usage of minimal and effective dosage of preservative in multivalent PCV was investigated. Microbial content and preservative efficacies were studied according to United States Pharmacopeia (USP) 'USP29, General Chapter 51'. Microorganisms count in test samples with different strengths of preservatives along with drug product (vaccine formulation) were checked from day 0 to $35^{th}$ day.

The inoculum with initial count of $1 \times 10^5$ to $1 \times 10^7$ cells of micro-organisms which are the most common contaminants (*Staphylococcus aureus, Pseudomonas aeruginosa*, a yeast *Candida albicans, Escherichia coli* and *Aspergillus brasiliensis*) were inoculated individually for evaluating the strength of each preservative.

In the current study, incubation of test samples with test organisms (Table 1) was carried out in LabTech™ incubator for a period of 35 days.

TABLE 1

Details of Test Organism

| S.No | Name of the Organism | Strain ID |
|---|---|---|
| 1. | *Candida albicans* | NCPF3139 |
| 2. | *Pseudomonas aeruginosa* | NCTC12924 |
| 3. | *Staphylococcus aureus* | NCTC10788 |
| 4. | *Escherichia coli* | NCTC12923 |
| 5. | *Aspergillus brasiliensis* | NCPF2275 |

Inoculum Determination

In the event of addition of known amount of population of different test organism into the test samples, Initially the test cultures were checked for the viability by serial diluting 1 mL of cryo-vial content from $10^1$ to $10^{-8}$ with sterile saline solution. From the last 6 dilutions 100 µL suspension was plated (Pour plate method) on suitable media plates and were incubated at optimal conditions. Post incubation period, plates were observed, and colonies were enumerated to find CFU/mL of each test organism.

TABLE 2

Incubation details

| Name of the organism | Suitable media | Incubation condition Temperature | Time (Hrs) |
|---|---|---|---|
| Candida albicans | Sabouraud Dextrose Agar (TSA) | 22.5 ± 2.5° C. | 44-72 |
| Pseudomonas aeruginosa | Soybean-Casein Digest Agar (SCDA) | 32.5 ± 2.5° C. | 18-24 |
| Staphylococcus aureus | | | 18-24 |
| Escherichia coli | | | 18-24 |
| Aspergillus brasiliensis | Sabouraud Dextrose Agar (SDA) | 22.5 ± 2.5° C. | 36-48 |

Based on the results obtained in the inoculum determination, the final volume of inoculum to be added to formulations was calculated to maintain the required final concentration as per compendial requirement.

As the product of interest for which the effective dose of antimicrobial substance to be established will fall under category-1 as per USP29 General Chapter 51, the volume of the suspension inoculum used is between 0.5% and 1.0% of the volume of the product.

TABLE 3

Details of inoculum Volume to be added

| Name of the organism | Volume of test sample | Volume of inoculum required | Approx. final conc. of cells in each test sample |
|---|---|---|---|
| Pseudomonas aeruginosa | 5 Ml | 100 μL | $1.9*10^6$ |
| Staphylococcus aureus | 5 mL | 100 μL | $1.4*10^6$ |
| Escherichia coli | 5 mL | 100 μL | $6*10^7$ |
| Candida albicans | 5 mL | 100 μL | $2*10^6$ |
| Aspergillus brasiliensis | 5 mL | 200 μL | $2*10^5$ |

Sample Preparation and Inoculum Addition

Initially, formulations were prepared without drug product to test the broad concentration range of preservative individually and in combination. Based on the results thereof experiments at lower concentration range of preservative individually and in combination with drug product was designed.

The concentration of test microorganisms that were added to the product are such that the final concentration of the test preparation after inoculation meets all the compendial requirements. These details are tabulated in Tables 4a and Table 4b.

TABLE 4a

Formulation Details (Without drug product)

| | Composition | | | | | |
|---|---|---|---|---|---|---|
| | 2-phenoxyethanol | | Metacresol | | $Al^{+++}$ Content | Saline (0.9% W/V) |
| S. No. | (%) | mg/ml | (%) | mg/mL | mg/mL | mg/mL |
| 1 | 0.2 | 2 | NA | | 1 | q.s |
| 2 | 0.4 | 4 | | | 1 | q.s |
| 3 | 0.6 | 6 | | | 1 | q.s |
| 4 | NA | | 0.05 | 0.5 | 1 | q.s |
| 5 | | | 0.1 | 1 | 1 | q.s |

TABLE 4a-continued

Formulation Details (Without drug product)

| | Composition | | | | | |
|---|---|---|---|---|---|---|
| | 2-phenoxyethanol | | Metacresol | | $Al^{+++}$ Content | Saline (0.9% W/V) |
| S. No. | (%) | mg/ml | (%) | mg/mL | mg/mL | mg/mL |
| 6 | | | 0.2 | 2 | 1 | q.s |
| 7 | | | 0.3 | 3 | 1 | q.s |
| 8 | 0.2 | 2 | 0.3 | 3 | 1 | q.s |
| 9 | 0.3 | 3 | 0.1 | 1 | 1 | q.s |
| 10 | 0.4 | 4 | 0.2 | 2 | 1 | q.s |
| 11 | 0.5 | 5 | 0.2 | 2 | 1 | q.s |
| 12 | 0.5 | 5 | 0.3 | 3 | 1 | q.s |
| 13 | 0.6 | 6 | 0.2 | 1 | 1 | q.s |
| 14 | 0.6 | 6 | 0.3 | 3 | 1 | q.s |
| 15 | 0.8 | 8 | 0.1 | 1 | 1 | q.s |

TABLE 4b

Formulations Details (With drug product)

| | Composition | | | | | |
|---|---|---|---|---|---|---|
| | 2-phenoxyethanol | | Metacresol | | $Al^{+++}$ Content | Saline (0.9% W/V) |
| S. No. | Percentage | mg/mL | Percentage | mg/mL | mg/mL | mg/mL |
| 1 | 0.3 | 3 | 0.1 | 1 | 1 | q.s |
| 2 | 0.3 | 3 | 0.05 | 0.5 | 1 | q.s |
| 3 | 0.3 | 3 | 0.025 | 0.25 | 1 | q.s |
| 4 | 0.3 | 3 | 0.005 | 0.05 | 1 | q.s |
| 5 | 0.3 | 3 | NA | | 1 | q.s |
| 6 | NA | | 0.05 | 0.5 | 1 | q.s |
| 7 | 0.2 | 2 | 0.05 | 0.5 | 1 | q.s |
| 8 | 0 | 0 | 0 | 0 | 1 | q.s |

Further based on the results of the inoculum determination process, known concentration of cells were inoculated into formulations with drug product samples. Post inoculation samples were incubated at respective temperatures, collected and serially diluted at appropriate intervals to determine number of viable cells present in each test sample.

Preservative Efficacy Tested Against *Staphylococcus aureus* and *Escherichia coli*

Formulations inoculated with *Staphylococcus aureus* showed more than 2 log reduction from initial cell count in all test samples and on 35th day showed no growth for all the compositions. Volume of sample used was 100 μL.

TABLE 5

Test results for *Staphylococcus aureus* (NCTC10788)

| Preservative | 0th day $10^5$ | Viability | 7th day $10^5$ | Viability | 28th day $10^5$ | Viability | 35th day $10^5$ | Viability |
|---|---|---|---|---|---|---|---|---|
| 2-PE 3 mg + m-C 1 mg | 196 | $1.9 * 10^8$ | 0 | 0 | 0 | 0 | 0 | 0 |
| 2-PE 3 mg + m-C 0.5 mg | 84 | $8.4 * 10^7$ | 11 | $1.1 * 10^7$ | 0 | 0 | 0 | 0 |
| 2-PE 3 mg + m-C 0.25 mg | 154 | $1.54 * 10^8$ | 0 | 0 | 0 | 0 | 0 | 0 |
| 2-PE 3 mg + m-C 0.05 mg | TNTC | NA | 0 | 0 | 0 | 0 | 0 | 0 |
| 2-PE 3 mg | 56 | $5.6 * 10^7$ | 1 | $1 * 10^6$ | 0 | 0 | 0 | 0 |
| m-C 0.5 mg | TNTC | NA | 9 | $9 * 10^6$ | 0 | 0 | 0 | 0 |
| 2-PE 2 mg + m-C 0.5 mg | 112 | $1.12 * 10^8$ | 0 | 0 | 0 | 0 | 0 | 0 |
| Placebo | 57 | $5.7 * 10^7$ | 0 | 0 | 0 | 0 | 0 | 0 |

2-PE = 2-phenoxyethanol; m-C = m-cresol

Formulations inoculated with *Escherichia coli* showed more than 2 log reduction in samples containing 2-PE 3 mg+m-C 1 mg; 2-PE 3 mg+m-C 0.5 mg; 2-PE 3 mg+m-C 0.25 mg and 2-PE 2 mg+m-C 0.5 mg; and with 2-PE 3 mg; m-C 0.5 mg and 2-PE 3 mg+m-C 0.05 mg; preservatives showed log reduction and few counts observed on 35th day.

TABLE 6

Test results for *Escherichia coli* (NCTC12923)

| Preservative | 0th day $10^5$ | Viability | 7th day $10^5$ | Viability | 28th day $10^5$ | Viability | 35th day $10^5$ | Viability |
|---|---|---|---|---|---|---|---|---|
| 2-PE 3 mg + m-C 1 mg | 188 | $1.88 * 10^8$ | 0 | 0 | 0 | 0 | 0 | 0 |
| 2-PE 3 mg + m-C 0.5 mg | 60 | $6.0 * 10^7$ | 1 | $1 * 10^6$ | 0 | 0 | 0 | 0 |
| 2-PE 3 mg + m-C 0.25 mg | 37 | $3.7 * 10^7$ | 9 | $9 * 10^6$ | 0 | 0 | 0 | 0 |
| 2-PE 3 mg + m-C 0.05 mg | 39 | $3.9 * 10^7$ | 28 | $2.8 * 10^7$ | 5 | $5 * 10^6$ | 0 | 0 |
| 2-PE 3 mg | 56 | $5.6 * 10^7$ | 43 | $4.3 * 10^7$ | 26 | $2.6 * 10^7$ | 1 | $1 * 10^5$ |
| m-C 0.5 mg | 131 | $1.31 * 10^8$ | 40 | $4.0 * 10^7$ | 103 | $1.03 * 10^8$ | 1 | $1 * 10^5$ |
| 2-PE 2 mg + m-C 0.5 mg | 49 | $4.9 * 10^7$ | 4 | $4 * 10^6$ | 0 | 0 | 0 | 0 |
| Placebo | TNTC | TNTC | 5 | $5 * 10^6$ | 122 | $1.22 * 10^8$ | 15 | $1.5 * 10^7$ |

2-PE = 2-phenoxyethanol; m-C = m-cresol

All the preservative compositions for *Staphylococcus aureus* and *Escherichia coli* met the compendial requirements.

Preservative Efficacy Tested Against *Pseudomonas aeruginosa* and *Candida albicans*

Formulations inoculated with *Pseudomonas aeruginosa* and *Candida albicans* showed more than 2 log reduction from initial cell count. *Pseudomonas aeruginosa* showed no growth for all the compositions except for the formulation not containing any preservative (Placebo). From 2nd day onwards there was no growth in all preservative compositions.

*Candida albicans* showed no growth for all the compositions from 12th day. From 2nd day onwards decrease in cell count were observed.

TABLE 7

Test results for *Pseudomonas aeruginosa* (NCTC12924)

| Preservative | 0th day $10^5$ | Viability | 7th day $10^5$ | Viability | 28th day $10^5$ | Viability | 35th day $10^5$ | Viability |
|---|---|---|---|---|---|---|---|---|
| 2-PE 3 mg + m-C 1 mg | 12 | $1.2 * 10^7$ | 0 | 0 | 0 | 0 | 0 | 0 |
| 2-PE 3 mg + m-C 0.5 mg | 63 | $6.3 * 10^7$ | 0 | 0 | 0 | 0 | 0 | 0 |

TABLE 7-continued

Test results for *Pseudomonas aeruginosa* (NCTC12924)

| Preservative | 0th day $10^5$ | Viability | 7th day $10^5$ | Viability | 28th day $10^5$ | Viability | 35th day $10^5$ | Viability |
|---|---|---|---|---|---|---|---|---|
| 2-PE 3 mg + m-C 0.25 mg | 62 | $6.3 * 10^7$ | 0 | 0 | 0 | 0 | 0 | 0 |
| 2-PE 3 mg + m-C 0.05 mg | 51 | $5.1 * 10^7$ | 0 | 0 | 0 | 0 | 0 | 0 |
| 2-PE 3 mg | 65 | $6.5 * 10^7$ | 0 | 0 | 0 | 0 | 0 | 0 |
| m-C 0.5 mg | 242 | $2.42 * 10^8$ | 0 | 0 | 0 | 0 | 0 | 0 |
| 2-PE 2 mg + m-C 0.5 mg | 31 | $3.1 * 10^7$ | 0 | 0 | 0 | 0 | 0 | 0 |
| Placebo | TNTC | NA | TNTC | NA | 300 | $3 * 10^8$ | 300 | $3 * 10^8$ |

2-PE = 2-phenoxyethanol; m-C = m-cresol

TABLE 8

Test results for *Candida albicans* (NCPF3139)

| Preservative | 0th day $10^5$ | Viability | 7th day $10^5$ | Viability | 28th day $10^5$ | Viability | 35th day $10^5$ | Viability |
|---|---|---|---|---|---|---|---|---|
| 2-PE 3 mg + m-C 1 mg | 3 | $3 * 10^5$ | 0 | 0 | 0 | 0 | 0 | 0 |
| 2-PE 3 mg + m-C 0.5 mg | 7 | $7 * 10^5$ | 1 | 0 | 0 | 0 | 0 | 0 |
| 2-PE 3 mg + m-C 0.25 mg | 7 | $7 * 10^5$ | 2 | $2 * 10^5$ | 0 | 0 | 0 | 0 |
| 2-PE 3 mg + m-C 0.05 mg | 6 | $6 * 10^5$ | 0 | 0 | 0 | 0 | 0 | 0 |
| 2-PE 3 mg | 4 | $4 * 10^5$ | 3 | $3 * 10^5$ | 0 | 0 | 0 | 0 |
| m-C 0.5 mg | 4 | $4 * 10^5$ | 0 | 0 | 0 | 0 | 0 | 0 |
| 2-PE 2 mg + m-C 0.5 mg | 4 | $4 * 10^5$ | 1 | $1 * 10^5$ | 0 | 0 | 0 | 0 |
| Placebo | 2 | $2 * 10^5$ | 1 | $1 * 10^5$ | 0 | 0 | 0 | 0 |

2-PE = 2-phenoxyethanol; m-C = m-cresol

All the preservative compositions for *Pseudomonas aeruginosa* and *Candida albicans* met the compendial requirements.

Preservative Efficacy Tested Against *Aspergillus brasiliensis*

*Aspergillus brasiliensis* showed no growth in all preservative compositions from 12th day onwards except the formulation which doesn't contain any preservative (placebo). From 2nd day onwards cell count reduction was observed in all the preservative compositions.

TABLE 9

Test results for *Aspergillus brasiliensis* (NCPF2275)

| Preservative | 0th day $10^5$ | Viability | 7th day $10^5$ | Viability | 28th day $10^5$ | Viability | 35th day $10^5$ | Viability |
|---|---|---|---|---|---|---|---|---|
| 2-PE 3 mg + m-C 1 mg | 25 | $2.5 * 10^7$ | 0 | 0 | 0 | 0 | 0 | 0 |
| 2-PE 3 mg + m-C 0.5 mg | 16 | $1.6 * 10^7$ | 0 | 0 | 0 | 0 | 0 | 0 |
| 2-PE 3 mg + m-C 0.25 mg | 86 | $8.6 * 10^7$ | 0 | 0 | 0 | 0 | 0 | 0 |
| 2-PE 3 mg + m-C 0.05 mg | 10 | $1.0 * 10^7$ | 3 | $3 * 10^6$ | 0 | 0 | 0 | 0 |
| 2-PE 3 mg | 18 | $1.8 * 10^7$ | 5 | $5 * 10^6$ | 0 | 0 | 0 | 0 |
| m-C 0.5 mg | 11 | $1.1 * 10^7$ | 5 | $5 * 10^6$ | 0 | 0 | 0 | 0 |
| 2-PE 2 mg + m-C 0.5 mg | 38 | $3.8 * 10^7$ | 0 | 0 | 0 | 0 | 0 | 0 |
| Placebo | 12 | $1.2 * 10^7$ | 6 | $6 * 10^6$ | 7 | $7 * 10^6$ | 5 | $5 * 10^6$ |

2-PE = 2-phenoxyethanol; m-C = m-cresol

All the preservative compositions for *Aspergillus brasiliensis* met the compendial requirements.

Based on the results it is evident that the formulation containing combined preservatives with 0.05% (0.05 mg/ml) of meta-Cresol and 0.2% (2 mg/ml) of 2-Phenoxy ethanol is efficacious in preventing microbial growth in final formulations.

Example 2: Formulation of a 14-Valent Pneumococcal Conjugate Vaccine (without Preservative)

| Conjugate serotype | Quantity (µg)/ dose (0.5 ml) |
|---|---|
| 1 | 2.2 |
| 3 | 2.2 |
| 4 | 2.2 |
| 5 | 2.2 |
| 6B | 4.4 |
| 7F | 2.2 |
| 9V | 2.2 |
| 14 | 2.2 |
| 18C | 2.2 |
| 19A | 2.2 |
| 19F | 2.2 |
| 22F | 2.2 |
| 23F | 2.2 |
| 33F | 2.2 |
| Excipients | |
| Succinic acid | 295 µg |
| Elemental aluminium as aluminium phosphate gel | 0.5 mg |
| poloxamer 188 | 1000 µg |
| 0.9% sodium chloride solution (w/v) | qs |

Example 3: Formulation of a 14-Valent Pneumococcal Conjugate Vaccine (with Preservative)

| Conjugate serotype | Quantity (µg)/ dose (0.5 ml) |
|---|---|
| 1 | 2.2 |
| 3 | 2.2 |
| 4 | 2.2 |
| 5 | 2.2 |
| 6B | 4.4 |
| 7F | 2.2 |
| 9V | 2.2 |
| 14 | 2.2 |

-continued

| Conjugate serotype | Quantity (µg)/dose (0.5 ml) |
|---|---|
| 18C | 2.2 |
| 19A | 2.2 |
| 19F | 2.2 |
| 22F | 2.2 |
| 23F | 2.2 |
| 33F | 2.2 |
| Excipients | |
| Succinic acid | 295 µg |
| Elemental aluminium as aluminium phosphate gel | 0.5 mg |
| poloxamer 188 | 1000 µg |
| 2-phenoxyethanol | 3 mg |
| m-cresol | 1 mg |
| 0.9% sodium chloride solution (w/v) | qs |

Given below is the process steps involved in manufacturing Formulation of a 14-Valent Pneumococcal Conjugate Vaccine.

Part quantity of saline was taken followed by addition of pneumococcal monovalent conjugate bulk (PnMBC). It was mixed for few minutes to get uniformity and then batch quantity of 10% sterile Poloxamer 188 solution was slowly added and again mixed for about 5 minutes for uniformity. This was followed by addition sterile filtered succinic acid stock solution, then 2-phenoxyethanol stock solution and metacresol stock solution. Mixed for few minutes and batch quantity of aluminium phosphate gel was added to the blend under continuous stirring. After mixing for few minutes, pH of the mixture was checked and adjusted to ~5.8±0.2 using 1N NaOH and volume make up was done with remaining part of saline. Blending was continued further for 2 hours at 200±50 RPM for adsorption to get final bulk.

Post sampling, both the vaccine bulks were aseptically and separately filled into vials inside laminar air flow unit, sampled the vials required for testing and remaining vials stored at 2-8° C. chamber.

Example 4: Formulation of Hexavalent Vaccine

| Each 0.5 ml dose of vaccine contains | Quantity/dose of 0.5 ml |
|---|---|
| Diphtheria toxoid (DT) | 25 Lf |
| Tetanus toxoid (TT) | 5 Lf |
| whole-cell *Bordetella pertussis* (wP) | 16 or 20 IOU |
| *Haemophilus influenzae* type B polysaccharide (Hib-PRP)-TT conjugate | 11 micrograms |
| Hepatitis B surface antigen (HepB) | 12.5 microgram |
| Inactivated poliomyelitis virus (IPV) | |
| Type 1 | 20 DU |
| Type 2 | 4 DU |
| Type 3 | 16 DU |
| Al content | 0.3 mg |
| 2-phenoxyethanol (2-PE) | 2 mg |
| m-Cresol | 1 mg |

The process steps involved in manufacturing the hexavalent formulation described above is given below:
 i. HepB antigen, diphtheria toxoid and tetanus toxoid were added to a blending vessel containing aluminium phosphate and the mixture was stirred for 12-16 hrs,
 ii. the pH of wP was adjusted to 6.8-7.2 and added to the DT-HepB mixture obtained in step (i), and the pH was adjusted to 6.2-6.5,
 iii. to the above DTwP-Hep B mixture, S19 IPV bulk antigen was added, followed by saline solution,
 iv. a solution of 2-PE was added and the mixture was cooled at 2-8° C.,
 v. to the mixture obtained in step (iv) HibTT was added,
 vi. the volume was adjusted with normal saline solution and filled the solution in individual containers.

Example 5: Formulation of a 14-Valent Pneumococcal Conjugate Vaccine (with Preservative)

| Conjugate serotype | Quantity (µg)/dose (0.5 ml) |
|---|---|
| 1 | 2.2 |
| 3 | 2.2 |
| 4 | 2.2 |
| 5 | 2.2 |
| 6B | 4.4 |
| 7F | 2.2 |
| 9V | 2.2 |
| 14 | 2.2 |
| 18C | 2.2 |
| 19A | 2.2 |
| 19F | 2.2 |
| 22F | 2.2 |
| 23F | 2.2 |
| 33F | 2.2 |
| Excipients | |
| Succinic acid | 295 µg |
| Elemental aluminium as aluminium phosphate gel | 0.5 mg |
| Polysorbate 20 | 100 µg |
| 2-phenoxyethanol | 3 mg |
| Benzyl alcohol | 2 mg |
| 0.9% sodium chloride solution (w/v) | qs |

Example 6: Formulation of a 14-Valent Pneumococcal Conjugate Vaccine (with Preservative)

| Conjugate serotype | Quantity (µg)/dose (0.5 ml) |
|---|---|
| 1 | 2.2 |
| 3 | 2.2 |
| 4 | 2.2 |
| 5 | 2.2 |
| 6B | 4.4 |
| 7F | 2.2 |
| 9V | 2.2 |
| 14 | 2.2 |
| 18C | 2.2 |
| 19A | 2.2 |
| 19F | 2.2 |
| 22F | 2.2 |
| 23F | 2.2 |
| 33F | 2.2 |
| Excipients | |
| Succinic acid | 295 µg |
| Elemental aluminium as aluminium phosphate gel | 0.5 mg |
| Polysorbate 80 | 100 µg |
| 2-phenoxyethanol | 3 mg |
| Benzoic acid | 2 mg |
| 0.9% sodium chloride solution (w/v) | qs |

Example 7: Formulation of a 14-Valent Pneumococcal Conjugate Vaccine (with Preservative)

| Conjugate serotype | Quantity (µg)/dose (0.5 ml) |
|---|---|
| 1 | 2.2 |
| 3 | 2.2 |
| 4 | 2.2 |
| 5 | 2.2 |
| 6B | 4.4 |
| 7F | 2.2 |
| 9V | 2.2 |
| 14 | 2.2 |
| 18C | 2.2 |
| 19A | 2.2 |
| 19F | 2.2 |
| 22F | 2.2 |
| 23F | 2.2 |
| 33F | 2.2 |
| Excipients | |
| Succinic acid | 295 µg |
| Elemental aluminium as aluminium phosphate gel | 0.5 mg |
| poloxamer 188 | 1000 µg |
| 2-phenoxyethanol | 3 mg |
| Phenol acid | 2 mg |
| 0.9% sodium chloride solution (w/v) | qs |

Example 8: Immunization of Rabbits with the Preservative Containing Formulation of PCV In order to ascertain whether the formulation containing preservative composition has any negative influence on serum antibody titer, vaccine formulation containing two preservatives was prepared (Example 2). Another formulation without any preservative but containing exactly the same excipient was prepared as 'control' (Example 3). These polysaccharide conjugates were adsorbed onto aluminum phosphate gel and assessed for critical vaccine quality attributes in accordance with the pharmacopoeial guidelines.

Healthy rabbits having weight of 1.5 to 2 kg each were bred and reared in a contained facility. Rabbits were immunized with the aforementioned formulation. Each group, consisting of 7 rabbits, were immunized with either Example 2 or Example 3 formulation on days 1, 15 and 29. Blood samples were collected on days 0 (pre-immune), 15 (test bleed) and 36 (final bleed). Rabbit sera collected on day 0 (PD1) and Day 40 (PD3) were analyzed for serotype specific immune response using ELISA. The ELISA was performed as per the WHO suggested protocol.

| | Schedule | |
|---|---|---|
| Group size | Immunization | Bleeding |
| 7 Rabbits each | Day 1, Day 15 & Day 29 | Day 0 (PI), Day 12, Day 26 & Day 40 (PD3) |

Titer Estimation

Antibody titer in the immunized animals was assigned as inverse of dilution factor that showed twice as much $OD_{450\ nm}$ as the pre-immune titer (approximately 0.2 OD). Serum antibody titer of each animal (n=7) was plotted using MedCalc on logarithmic scale (on y-axis). The error bar indicates variance at 95% Confidence Interval (CI). The mid-point in the error bar represents the group average serum antibody titer.

Figure 2A:
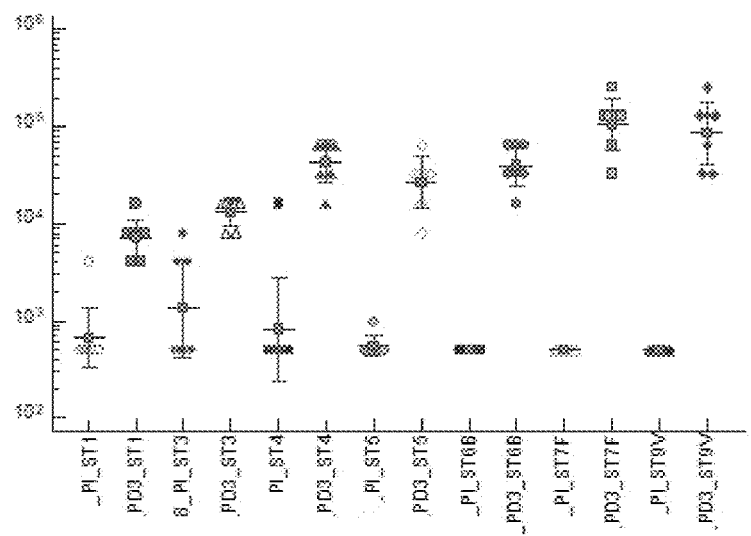
FIGS. 2A&B depicts serum antibody titers in rabbit immunized with formulation without preservative (Example 2).
Figure 2B:
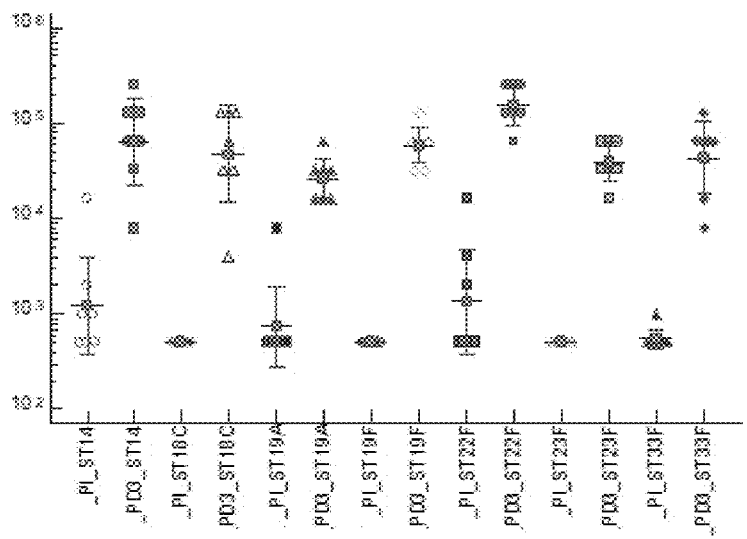

A guide to reading the plot is given below which describes how the plot is laid out (FIG. 1). Briefly, the x-axis legend contains the Formulation ID, bleed analyzed, and the serotype tested. For example, PI_ST1 means, serum antibody titer in rabbit immunized with formulation disclosed in Example 2 at pre-immune bleed against Serotype 1, PD3_ST1 means, serum antibody titer in rabbit immunized with formulation disclosed in Example 2 at post dose 3 bleed against Serotype 1, PD3_ST22F means, serum antibody titer in rabbit immunized with formulation disclosed in Example 2 at post dose 3 bleed against Serotype 22F and so on (FIGS. 2 A & B). It is common to expect background titers in the pre-immune rabbits. However, post third dose of immunization the serum antibody titer increases several-fold indicating robust and specific immune response in the immunized animals.

Figure 3A:
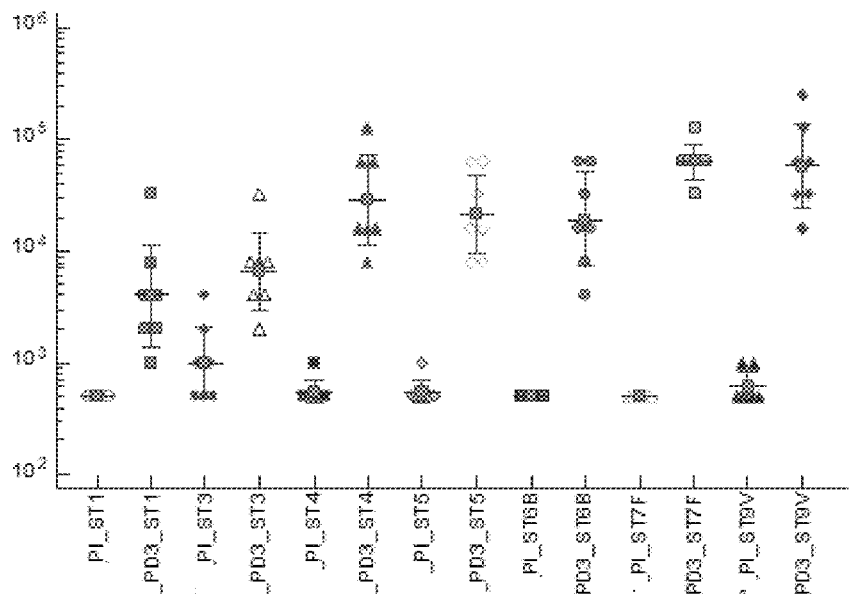
FIGS. 3A&B depicts serum antibody titers in rabbit immunized with formulation containing preservative system (Example 3).
Figure 3B:
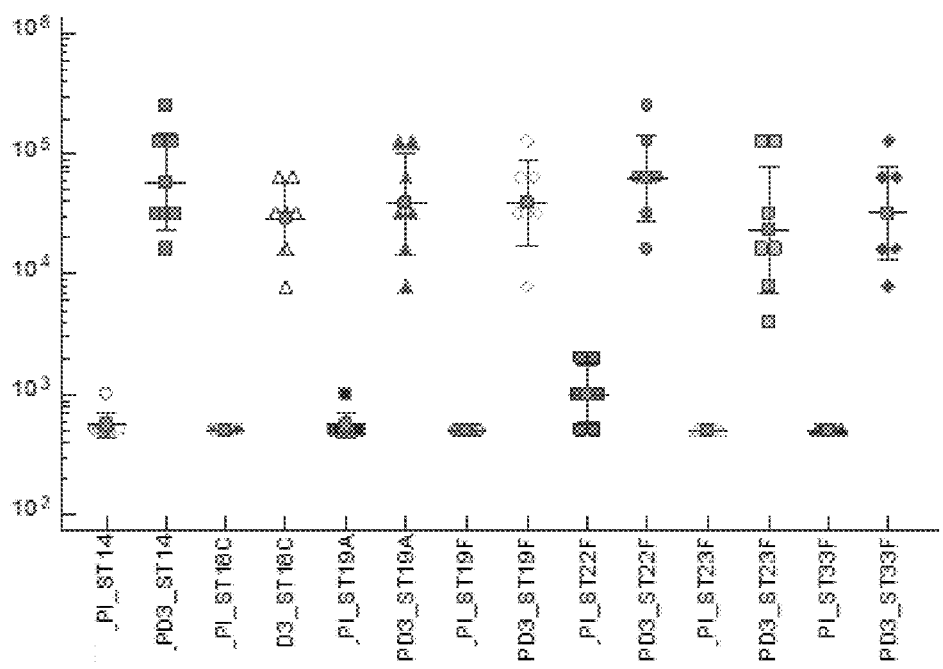

Similarly, PI_ST1 in FIGS. 3 A & B means, serum antibody titer in rabbit immunized with formulation disclosed in example 3 at pre-immune bleed against Serotype 1, PD3_ST1 means, serum antibody titer in rabbit immunized with formulation disclosed in example 3 at post dose 3 bleed against Serotype 1, PD3_ST22F means, serum antibody titer in rabbit immunized with formulation disclosed in example 3 at post dose 3 bleed against Serotype 22F and so on. It is observed that the serum antibody titers in rabbit immunized with formulation described in example 3 was similar to those observed in rabbits immunized with formulation disclosed in example 2. Hence, the data herein indicates that the presence of preservative composition has no negative effect on immunogenicity of the vaccine formulation.

The concentration of preservative chosen to test the immune response was 0.6 mg/ml of 2-PE and 0.2 mg/mL of m-cresol. As shown in the figures, there is no inhibitory effect on the immune response in rabbits at this concentration of preservatives and it is expected that the concentrations lower than this will not have any negative effect on the immune response too.

We claim:

1. A vaccine formulation comprising (a) an antigen; and (b) a preservative system comprising 2-phenoxyethanol at a concentration in the range of 0.1% to 0.2% and m-cresol at a concentration in the range of 0.005% to 0.05%.

2. The vaccine formulation of claim 1, comprising one or more pharmaceutically acceptable carriers.

3. The vaccine formulation of claim 1, wherein the vaccine formulation is a monovalent vaccine or a multivalent combination vaccine.

4. The vaccine formulation of claim 3, wherein the vaccine formulation is a monovalent vaccine formulation comprising an antigen selected from the group consisting of *Streptococcus pneumonia* (Pneumococcal capsular polysaccharide), *Neisseria meningitides* (Men A, C, W-135, X or Y), *Salmonella typhi* (Vi), *Salmonella* paratyphi (O:2), *Haemophilus* influenza (Hib-PRP), *Corynebacterium* Diptheriae (Diptheriae Toxoid-DT), *Bordetella pertussis* (wP/aP), *Clostridium tetani* (Tetanus Toxoid), Hepatitis A Virus (HAV), Hepatitis B Virus (HBV), Hepatitis C Virus (HCV), Inactivated Japanese Encephalitis Virus, Rabies Virus and Inactivated Poliomyelitis Virus.

5. The vaccine formulation of claim 3, wherein the vaccine formulation is a multivalent vaccine formulation selected from the group consisting of a bivalent vaccine, a trivalent vaccine, a tetravalent vaccine, a pentavalent vaccine, a hexavalent vaccine and a multivalent pneumococcal conjugate vaccine.

6. The vaccine formulation of claim 5, wherein the bivalent vaccine is selected from the group consisting of Td vaccine, Vi:O2 conjugate and MR;
   wherein the trivalent vaccine is selected from the group consisting of DTwP, Vi:O2-HepA and MMR;
   wherein the tetravalent vaccine is selected from the group consisting of DTwP-Hib, DTaP-Hib, DTwP-IPV, DTwP-HepB, ACW-135Y;
   wherein the pentavalent vaccine is selected from the group consisting of DTwPHib-HepB and DTaPHib-HepB;
   and wherein the hexavalent vaccine is selected from the group consisting of DTwPHib-HepB-IPV and DTaPHib-HepB-IPV.

7. The vaccine formulation of claim 1, wherein the pneumococcal conjugate vaccine comprises one or more pneumococcal capsular polysaccharide protein conjugates and optionally, one or more pharmaceutically acceptable carriers.

8. The vaccine formulation of claim 7, wherein the one or more pneumococcal capsular polysaccharide protein conjugates comprise *Streptococcus pneumonia* capsular polysaccharides selected from the group consisting of serotypes 1, 2, 3, 4, 5, 6A, 6B, 6C, 6D, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45,
   and wherein each capsular polysaccharide is conjugated to a carrier protein selected from PsaA, $CRM_{197}$, diphtheria toxoid (DT), tetanus toxoid (TT), pertussis toxoid, cholera toxoid and *Haemophilus influenzae* protein D.

9. The vaccine formulation of claim 8, wherein the preservative composition comprises at least one other preservative selected from the group consisting of benzyl alcohol at a concentration in the range of 0.01% to 1% and benzoic acid at a concentration in the range of 0.01% to 1%, and wherein the vaccine formulation further comprises one or more pharmaceutically acceptable carriers or excipients.

10. The vaccine formulation of claim 9, wherein the vaccine formulation is selected from one of the following:
   a. a 14 valent pneumococcal capsular polysaccharide protein conjugate vaccine comprising capsular polysaccharides from *Streptococcus pneumoniae* serotypes 1, 3, 4, 5, 6B, 7F, 9V, 14, 18C, 19A, 19F, 22F, 23F and 33F;
   b. a 20 valent pneumococcal capsular polysaccharide protein conjugate vaccine comprising capsular polysaccharides from *Streptococcus pneumoniae* serotypes 1, 3, 4, 5, 6A, 6B, 6C/6D, 7F, 9V, 11A, 12F, 14, 15A, 18C, 19A, 19F, 22F, 23A, 23F and 35B;
   c. a 20 valent pneumococcal capsular polysaccharide protein conjugate vaccine comprising capsular polysaccharides from *Streptococcus pneumoniae* serotypes 1, 3, 4, 5, 6A, 6B, 6C/6D, 7F, 9V, 14, 15A, 15C, 18C, 19A, 19F, 23A, 23B, 23F, 24F and 35B; and
   d. a 24 valent pneumococcal capsular polysaccharide protein conjugate vaccine comprising capsular polysaccharides from *Streptococcus pneumoniae* serotypes 1, 3, 4, 5, 6A, 6B, 7F, 8, 9V, 10A, 11A, 12F, 14, 15A, 18C, 19A, 19F, 22F, 23A, 23B, 23F, 24F, 33F and 35B.

* * * * *